United States Patent [19]

Casagrande et al.

[11] Patent Number: 5,073,547

[45] Date of Patent: Dec. 17, 1991

[54] DOPAMINE PRO-DRUG

[75] Inventors: Cesare Casagrande, Arese; Francesco Santangelo, Milan, both of Italy

[73] Assignee: Simes Societa Italiana Medicinali e Sintetici S.p.A., Vicenza, Italy

[21] Appl. No.: 512,211

[22] Filed: Apr. 20, 1990

[30] Foreign Application Priority Data

Apr. 20, 1989 [IT] Italy .................. 20209 A/89
Apr. 20, 1989 [IT] Italy .................. 20210 A/89

[51] Int. Cl.$^5$ ................ A61K 31/275; A61K 31/135; C07C 255/50; C07F 9/02
[52] U.S. Cl. .................. 514/79; 514/80; 514/94; 548/112; 548/413; 558/170; 558/174
[58] Field of Search ............... 558/170, 174; 548/413, 548/112; 514/79, 80, 94

[56] References Cited

U.S. PATENT DOCUMENTS

| | | | |
|---|---|---|---|
| 3,132,171 | 5/1964 | Plant | 558/110 |
| 3,891,696 | 6/1975 | Bodor et al. | 560/38 |
| 4,618,484 | 10/1986 | Pawelek | 514/110 |
| 4,663,349 | 5/1987 | Repta | 514/535 |
| 4,695,449 | 9/1987 | Pawelek | 514/110 |

FOREIGN PATENT DOCUMENTS 0216881 12/1984 European Pat. Off. .
0167204 1/1986 European Pat. Off. .

Primary Examiner—Johann Richter
Attorney, Agent, or Firm—Berman & Aisenberg

[57] ABSTRACT

A monophosphorylated L-dopa ester of formula

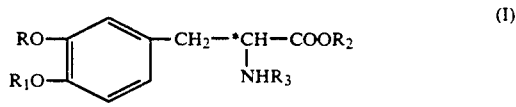

(wherein the asterisk, R, $R_1$, $R_2$ and $R_3$ have the meanings shown in the description),
salts thereof with pharmaceutically acceptable acids or bases, a process for the preparation thereof and a pharmaceutical composition containing said compound or a salt thereof are described.

The compound of formula I and the salts thereof are useful in the treatment of Parkinson's disease, renal failure, heart failure and hypertension.

5 Claims, No Drawings

DOPAMINE PRO-DRUG

DESCRIPTION

The present invention relates to dopamine pro-drugs and, more particularly, to monophosphorylated L-dopa esters having high bioavailability by oral route.

It is known that dopamine is an endogenous catecholamine endowed with important pharmacological effects. However, owing to unfavorable pharmacodynamic profile, dopamine is not therapeutically useful when administered to animals.

It is also known that L-dopa, i.e. L-3,4-dihydroxyphenylalanine, is a precursor of dopamine and that L-dopa is used in therapy for the treatment of Parkinson's disease. L-dopa, which is pharmacologically inert as such, is rapidly absorbed from the small bowel by an active transport system for aromatic aminoacids. Since about 95% of orally administered L-dopa is rapidly decarboxylated in the periphery to dopamine which does not penetrate the blood-brain barrier, large doses must be taken to allow sufficient accumulation of L-dopa in the brain, where its decarboxylation raises the central dopamine concentration required in the therapy of Parkinson's disease. Alternatively, the concurrent administration of peripherally acting inhibitors of L-dopa decarboxylase can reduce the required dose of L-dopa (Goodman and Gilman "The Pharmacological Basis of Therapeutics", 7th Ed., page 475 to 480, Macmillan Publishing Company, N.Y.). In order to inhibit peripheral decarboxylation, it has also been recommended (i) to incorporate L-dopa or a derivative thereof capable of being cleaved enzymatically in vivo to yield L-dopa in enteric-coated pharmaceutical formulations comprising an effervescent base (UK-A-1,485,676) or (ii) to use some specific pro-drugs of L-dopa via oral (U.S. Pat. No. 3,891,696; EP-A-0 309 827) or rectal route (U.S. Pat. No. 4,663,349).

In turn, EP-B$_1$-0 167 204 teaches improving absorption of catecolamines by phosphorylation of one hydroxy phenol group thereof. L-dopa, however, is not a catecolamine and its major drawback is peripheral decarboxylation rather than absorption.

In addition, U.S. Pat. No. 3,132,171 discloses that dopadiphosphate is watersoluble and stable in aqueous solutions while the pharmacodynamic profile of dopa seems to remain unaffected.

Finally, U.S. Pat. Nos. 4,618,484 and 4,695,449 disclose mono-and di-phosphorylated derivatives of dopa and pharmaceutically acceptable salts thereof in the treatment of melanomas wherein the phosphorous is the $^{32}$P isotope.

We have now surprisingly found that phosphorylation of one hydroxy phenol group of some L-dopa esters affords new dopamine pro-drugs which are endowed with a high bioavailability by oral route.

Although the reason for this improvement is still unknown, a decrease in peripheral decarboxylation could account for said improved bioavailability.

It is an object of this invention to provide a monophosphorylated L-dopa ester of the formula

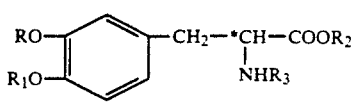
(I)

wherein
the asymmetric carbon atom marked with an asterisk has S configuration, and either R or R$_1$ is hydrogen and the other one is a group of the formula

wherein
R$_4$ is hydrogen, phenyl, alkylphenyl or a C$_1$-C$_6$ alkyl optionally substituted by one to three groups selected from hydroxy, alkoxy acyloxy, amino, carboxy or alkoxycarbonyl;

R$_2$ is a straight or branched C$_1$-C$_4$ alkyl, a C$_3$-C$_6$ cycloalkyl or a phenylalkyl having from 1 to 4 C atoms in the alkyl portion optionally substituted by 1 to 3 substituents selected from halogens, C$_1$-C$_3$ alkoxy and C$_1$-C$_3$ alkyl;

R$_3$ is hydrogen or an acyl group of a natural alpha-amino acid selected from glycine, alanine, valine, leucine, isoleucine, serine, threonine, cysteine, cystine, methionine, proline, hydroxyproline, phenylalanine, tyrosine, tryptophan, arginine, lysine, and histidine, optionally N-acylated by a C$_1$-C$_4$ acyl, or an acyl group of a natural amino acid ester of the formula

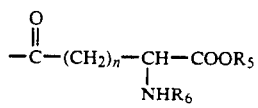

or

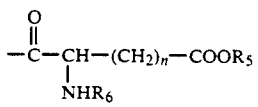

wherein
n is 1 or 2;
R$_5$ is hydrogen or a C$_1$-C$_3$ acyl;
R$_6$ is hydrogen or a C$_1$-C$_4$ acyl;
and the salts thereof with pharmaceutically acceptable acids or bases.

As used herein, the term "natural amino acid" means those aminoacids wherein the possible asymmetric carbon atom has S configuration.

Examples of suitable pharmaceutically acceptable acids are hydrochloric, hydrobromic, phosphoric, sulfuric, lactic, succinic, tartaric, acetic, salicylic, citric, benzoic, p-hydroxybenzoic, naphthalene-2-sulfonic, adipic and pimelic acid.

Examples of suitable pharmaceutically acceptable bases are sodium, potassium, calcium, magnesium and ammonium hydroxide, ethanolamine and tromethamol.

The compounds of this invention are useful in the treatment of renal failure, Parkinson's disease, heart failure and hyper tension and may be administered orally.

Preferred meanings of R$_4$ according to this invention are hydrogen, methyl, ethyl, isopropyl, phenyl and benzyl.

Preferred meanings of R$_2$ are methyl, ethyl, isopropyl, butyl, isobutyl, cyclopentyl cyclohexyl, 2-phenylethyl and 3-(4-methoxy-pheny)-propyl.

Preferred meanings of $R_3$ are hydrogen or an acyl group of a natural alpha-aminoacid selected from glycine, alanine, leucine and methionine, or an acyl group of an ester of a natural acidic aminoacid of the formula

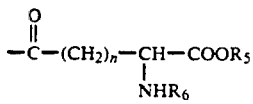

wherein
n is 2 and
$R_6$ is hydrogen.

Whenever not differently stated, acyl means an acyl group of an aliphatic carboxylic acid having from 1 to 5 carbon atoms or benzoyl.

Another object of this invention is to provide a process for the preparation of a compound of formula I and the salts thereof, comprising (i) phosphorylating an L-dopa ester of formula IIa optionally protected at one hydroxy phenol group and, when $R_3$ is hydrogen, at the amino group

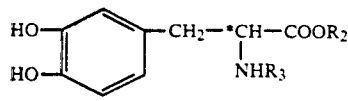

wherein the asterisk, $R_2$ and $R_3$ have the above mentioned meanings, with a suitable phosphorylating agent, (ii) removing the protective groups, if any, to yield a monophosphorylated L-dopa ester of the formula

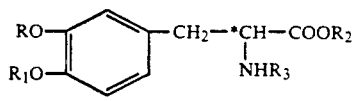

wherein the asterisk, R, $R_1$ and $R_2$ have the above mentioned meanings, (iii) optionally reacting a monophosphorylated L-dopa ester of formula I (wherein $R_3$ is hydrogen) with an optionally protected and N-acylated natural alpha-amino acid or with a natural acidic amino acid of the formula

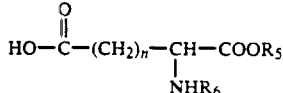

or

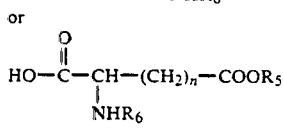

wherein n, $R_5$ and $R_6$ have the above mentioned meanings; and (iii) removing the protective groups, if any, to yield a compound of formula I, and (iv) if desired, adding a pharmaceutically acceptable acid or base to a compound of formula I to yield the corresponding pharmaceutically acceptable salt.

Step (i) is preferably carried out in a suitable solvent at a temperature of from $-80°$ C. to $+100°$ C.

Typical examples of suitable solvents are the phosphorylating agent itself and the inert organic solvents such as hydrocarbons, halocarbons, ethers, esters, amides, tertiary and heterocyclic amines.

When phosphorylation releases acidic compounds, step (i) is preferably carried out in the presence of suitable acid acceptors such as alkali and earth-alkaline carbonates or bicarbonates or tertiary and heterocyclic amines, such as triethylamine and pyridine, which may also act as the solvent.

Alternatively, in order to neutralize the acidic compounds released during the phosphorylation step, the phenol hydroxy group to be phosphorylated can be salified in advance with a base such as sodium hydride, sodium methylate or potassium t.butylate.

Depending on the phosphorylating agent and method which is used, phosphorylation yield compounds wherein $R_4$ is hydrogen (hereinafter called phosphoric monoesters) or wherein $R_4$ is different from H (hereinafter called phosphoric diesters).

In the preparation of phosphoric monoesters, preferred phosphorylating agents are orthophosphoric, pyrophosphoric and polyphosphoric acids, phosphorus pentoxide, chlorophosphoric acids, phosphoryl chloride and bromide, from which phosphoric monoesters are obtained directly or after an optional hydrolysis with water at the end of the phosphorylation reaction; other suitable phosphorylating agents having protective groups to be removed at the end of the phosphorylation reaction are dibenzyl- or diphenyl-phosphochloridate and 2-chloro-2-oxo-1,3,2-benzodioxaphosphate, the protective groups being removable by hydrogenolysis and oxidation, respectively, or 4,5-dimethyl-2-(1-imidazolyl)-2-oxo-1,3,2-dioxaphosphate; 2-cyanoethyl-phosphate and dibenzylphosphate require the addition of a suitable condensing agent such as N,N-dicyclohexylcarbodiimide.

Phosphoric diesters can be prepared both by direct phosphorylation or by alkylation of the corresponding monoesters.

In case of direct phosphorylation, preferred phosphorylating agents are the phosphodichloridates of the formula

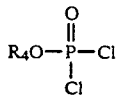

and phosphochloridates of the formula

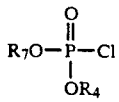

(wherein $R_7$ has the same meaning of $R_4$ or is a benzyl group); that at the end of the phosphorylation reaction require the removal of the chlorine atom or of the protective group $OR_7$ by hydrolysis or hydrogenolysis.

In the case of alkylation, a phosphoric monoester is reacted with an alcohol of the formula

Alternatively, a phosphoric diester, preferably in the form of an alkali-metal or silver salt, carrying benzyl as a protective group, can be alkylated with an alkylating agent of the formula

R₄X (wherein)

X is a halogen atom, an alkylsulphonyloxy or an arylsulphonyl oxy group); and then removing (by hydrogenolysis) the benzyl protective group.

Before step (i), protection of the compound IIa is preferably performed at the amino group, when $R_3$ is hydrogen and also at one of the two phenol hydroxy groups. The purpose of the latter protection is to direct phosphorylation on the free hydroxy group only, so avoiding formation of isomer mixtures.

In a similar way, the amino group (NH₂) of the natural alpha-amino acid or of compound III and IV is also preferably protected before performing step (iii) or when preparing compound IIa.

The artisan will recognize that all the protection and deprotection steps optionally performed in the process of this invention can be carried out according to conventional techniques of peptide chemistry.

The artisan will also recognize that compound IIa can easily be prepared with conventional techniques of step (iii).

The process of this invention is substantially similar to that of EP-B₁-0 167 204 which is therefore incorporated herein by reference.

When step (i) is carried out without protecting one of the two hydroxy phenol groups of compound IIa, a mixture mainly consisting of the two monophosphorylated products, 3- and 4-monophosphate, is obtained.

The two regioisomers may be separated by chromatography or crystallization.

The compounds of the present invention are orally adsorbed and metabolically generate dopamine thus producing useful pharmacological effects via stimulation of dopaminergic receptors.

The compounds of the present invention proved to have a vasodilating effect on the renal district in anesthetized dogs at a dose of 0.1–50 mg/kg i.p.

Mongrels of both sexes anesthetized with sodium pentobarbital (35 mg/kg i.v.) were used.

Artificial respiration was accomplished by means of a endotracheal tube with a Starling Ideal pump at a ventilation frequency of 16–18 cycles/minute, a flow rate of 16–17 ml/kg in order to obtain pO₂, pCO₂, and pH values of arterial blood of 85–100 mmHg, 30–40 mmHg and 7.35–7.45, respectively (Radiometer Copenhagen BMS 3 MK 2 Blood Microsystem Blood Gas Analyzer). Duodenum was insulated by abdomen incision and a polyethylene catheter was inserted for administering the drug. Left renal artery was isolated retroperitoneally, an electromagnetic transducer and a pneumatic obturator were positioned around the vessel to measure mechanical zero and blood flow, respectively.

Hemodynamic parameters were recorded on a Gould Brush MK 200 Graph Recorder while the pressure catheters were connected to a Bell and Howell Pressure Transducers and the electromagnetic flow transducer was connected to a Biotronex BL 613 Flowmeter.

Moreover, the compounds of formula I proved to have an antagonist action on the motility depression induced by reserpine (4 mg/kg ip) in mouse pretreated 16 hours before with iproniazid (150 mg/kg os) at a dose of 50–600 mg/kg i.p. (Wintroub B. V. et al, Am. J. Physiol. 217, 1716, 1969).

The compounds of this invention are useful in the therapy of Parkinson's disease and of cardiovascular diseases such as heart failure, hypertension and renal failure.

Another object of the present invention is therefore to provide pharmaceutical compositions containing one or more compounds of formula I or their pharmaceutically acceptable salts optionally together with one or more excipients suitable for pharmaceutical use.

The compositions of the present invention may be solid, such as tablets, granules, pills, capsules, or liquid, such as solutions, syrups, emulsions, and are prepared according to conventional methods.

They may be administered both enterally and parenterally. The preferred administration way is the oral route.

The doses may vary depending on the selected pharmaceutical form and the individual response of the patient, but usually are in the range of from 100 mg to 5 g per day.

The following examples are provided in order to better illustrate the present invention without, however, limiting it.

EXAMPLE 1

Preparation of 3-O-benzyl and 4-O-benzyl-N-benzyloxycarbonyl-L-dopa ethyl ester

A solution of N-benzyloxycarbonyl-L-dopa ethyl ester (135 g; 0.375 moles), benzyl chloride (94.94 g; 0.75 moles) and sodium bicarbonate (94.5 g; 1.125 moles) in absolute ethyl alcohol (1.35 l) is refluxed for 8 hours.

The salts are filtered off and the reaction mixture is kept at 5° C. overnight.

A solid separates, namely N-benzyloxycarbonyl-3,4-O-dibenzyl-L-dopa ethyl ester which is filtered.

The solution is evaporated to dryness and the two isomers 3-O-benzylether and 4-O-benzylether are separated by chromatography on silica gel column (eluent, CH₂Cl₂; CH₃CN=86:4).

From the fractions containing the less polar product, N-benzyloxycarbonyl-3-O-benzyl-L-dopa ethyl ester is obtained, m.p. 74°–75° C. (isopropyl ether).

¹H-NMR (300 MHz, CDCl₃) delta (ppm); 1.23 (3H, t); 2.97–3.10 (2H, m); 4.07–4.12 (2H, m); 4.57–4.62 (1H, m); 5.02 (2H, s); 5.11 (2H, d); 6.62 (1H, dd); 6.71 (1H, d); 6.85 (1H, d); 7.29–7.42 (10H, m).

From fractions containing the more polar product, N-benzyloxycarbonyl-4-O-benzyl-L-dopa ethyl ester is obtained as chromatographically pure oil (thin layer chromatography, eluent, CH₂Cl₂: CH₃CN=96:4, I₂ vapours detection).

¹H-NMR (300 MHz, CDCl₃) delta (ppm): 1.26 (3H, t); 3.03 (2H, d); 4.18 (2H, q); 4.55–4.62 (1H, m); 5.09 (4H, d); 6.57 (1H, dd); 6.7 (1H, d); 6.82 (1H, d); 7.28–7.42 (10H, m).

EXAMPLE 2

Preparation of 3-O-benzyl-N-benzyloxycarbonyl-L-dopa

NaOH 10N (8.9 ml; 89 mmoles) is added to a solution of 3-O- benzyl-N-benzyloxycarbonyl-L-dopa ethyl ester (20 g; 44.5 mmoles), prepared as described in Example 1, in absolute ethyl alcohol (200 ml) at a temperature of 5°–10° C.

The reaction mixture is diluted with water (20 ml) and is kept under stirring at room temperature for 9 hours.

Concentrated HCl is added and the sodium chloride which separates is removed by filtration; the solution is then concentrated under reduced pressure, diluted with ethyl acetate and washed with water. After drying on sodium sulfate, the solvent is evaporated and the oily residue crystallized from a mixture of isopropyl ether and petroleum ether. m.p. 85°–88° C.

Mass spectrum (chemical ionization, positive ions, ionization gas: ammonia) m/e 439 (M+ +1+NH$_3$ adduct).

EXAMPLE 3

Preparation of 3-O-benzyl-N-benzyloxycarbonyl-L-dopa n.butyl ester

A solution of 20% tetramethylammonium hydroxyde (5.95 g; 13.1 mmoles) in methyl alcohol is added to a solution of 3-O-benzyl-N-benzyloxycarbonyl-L-dopa (5 g; 11.9 mmoles) in methyl alcohol (50 ml). The solvent is removed under reduced pressure; the residue is dissolved in dimethylformamide (50 ml) and n.butyl iodide (4.6 g ; 25 mmoles) is added. After three hours at room temperature under stirring, the solution is washed with water and extracted with ethyl ether. The organic layer is separated, washed with water, dried on sodium sulfate and evaporated to dryness. The residue is purified by chromatography on silica gel column (eluent, CH$_2$Cl$_2$). The title compound is thus obtained as a chromatographically pure oil (thin layer chromatography - eluent, CH$_2$Cl$_2$:CH$_3$CN=95:5, I$_2$ vapours detection).

Mass spectrum (chemical ionization, negative ions, ionization gas : ammonia) m/e 476 (M+ −1), 386 (M+ - C$_7$H$_7$).

Working in a similar manner the following product, have been prepared:

3-O-benzyl-N-benzyloxycarbonyl-L-dopa 2-phenylethyl ester: chromatographically pure oil (thin layer chromatography eluent, CH$_2$Cl$_2$: CH$_3$CN=95:5, I$_2$ vapours detection).

Mass spectrum (chemical ionization, positive ions, ionization gas : isobutane) m/e 526 (M+ +1).

3-O-benzyl-N-benzyloxycarbonyl-L-dopa cyclohexyl ester: chromatographically pure oil (thin layer chromatography eluent, CH$_2$Cl$_2$:CH$_3$CN=95:5, I$_2$ vapours detection).

Mass spectrum (chemical ionization, positive ions, ionization gas: isobutane) m/e 464 (M+ +1).

3-O-benzyl-N-benzyloxycarbonyl-L-dopa cyclohexyl ester

Thionyl chloride (5,07 g; 42,6 mmoles) is added to a solution of 3-0-benzyl-N-benzyloxycarbonyl-L-dopa (6 g; 14.2 mmoles) in cyclohexyl alcohol (60 ml) at 0°–5° C. After 30 hours at room temperature, the reaction mixture is evaporated to dryness and washed as described for the preparation of 3-O-benzyl-N-benzyloxycarbonyl-L-dopa n.butyl ester. The product is obtained as a chromatographically pure oil (thin layer chromatography - eluent, CH$_2$Cl$_2$:CH$_3$CN=96:4, I$_2$ vapours detection).

Mass spectrum (chemical ionization, positive ions, ionization gas: isobutane) m/e 504 (M + +1).

EXAMPLE 4

Preparation of N-benzyloxycarbonyl-3-benzyloxy4-dibenzylphosphonyloxy-L-phenylalanine ethyl ester A suspension of 60% NaH in mineral oil (1.8 g; 45 mmoles) is added at 0°–5° C. to a solution of N-benzyloxycarbonyl-3-O-benzyl-L-dopa ethyl ester (18.5 g; 41 mmoles), prepared as described in Example 1, in dimethylformamide (185 ml).

After one hour at this temperature, a solution of dibenzyl phosphochloridate (14.53; 49 mmoles) in toluene (145 ml) is added dropwise.

After a further 30 minutes, acetic acid is added (2 ml); the reaction mixture is diluted with water, toluene is separated and the aqueous phase is extracted with ethyl ether.

The combined organic phases are washed with water and dried on Na$_2$SO$_4$.

After solvent evaporation, the residue is purified by chromatography on silica gel column (eluting with CH$_2$Cl$_2$ with increasing quantities of ethyl acetate up to 10%).

N-benzyloxycarbonyl-3-benzyloxy-4-dibenzylphosphonyloxy-L-phenylalanine ethyl ester is thus obtained in the form of pure oil (thin layer chromatography; eluent, CH$_2$Cl$_2$:ethyl acetate=9:1, I$_2$ vapours detection).

$^1$H-NMR (300 MHz, CDCl$_3$) delta (ppm): 1.21 (3H, t); 3.0–3.11 (2H, m); 4.05–4.18 (2H, m); 4.58–4.66 (1H, m); 4.95–5.11 (8H, m); 6.64 (1H, dd); 6.77 (1H, d); 7.12 (1H, dd); 7.18-7.39 (21H, m).

Working in a similar manner the following compounds have been obtained:

N-benzyloxycarbonyl-4-benzyloxy-3-dibenzylphosphonyloxy-L-phenylalanine ethyl ester as a chromatographically pure oil (thin layer chromotography - eluent, CH$_2$Cl$_2$:ethyl acetate=9:1, I$_2$ vapours detection).

$^1$H-NMR (300 MHz, CDCl$_3$) delta (ppm): 1.22 (3H, t); 2.92–3.08 (2H, m); 4.15 (2H, q); 4.55 (1H, m); 5.01–5.11 (8H, m); 6.86 (2H, s); 7.88 (1H, s); 7.18–7.42 (21H, m).

N-benzyloxycarbonyl-3-benzyloxy-4-ethylphosphonyloxy-L-phenylalanine ethyl ester as a chromatographically pure oil (thin layer chromatography - eluent, CH$_2$Cl$_2$:methanol:water:acetic acid=49:15:1:1, I$_2$ vapours detection).

$^1$H-NMR (300 Mhz, DMSO-d$_6$) delta (ppm): 0.99 (3H, t); 1.11 (3H, t); 2.72–2.96 (2H, m); 3.78 (2H, m); 3.78 (2H, quintet); 4.05 (2H, q); 4.14–4.22 (1H, m); 4.97–5.02 (2H, m); 6.68 (1H, dd); 6.95 (1H, d); 7.26–7.43 (11H, m).

N-benzyloxycarbonyl-3-benzyloxy-4-dibenzylphosphonyloxy-L-phenylalanine n.butyl ester as a chromatographically pure oil (thin layer chromotography - eluent, petroleum ether: ethyl acetate=65:35, I$_2$ vapours detection).

$^1$H-NMR, (300 MHz, CDCl$_3$) delta (ppm): 0.92 (3H, t); 1.23–1.38 (2H, m); 1.52–1.62 (2H, m); 3.05 (2H, t); 4.00–4.15 (2H, m); 4.62 (1H, dd); 4.95 (2H, s); 5.02 (2H, s); 5.06 (2H, s); 5.10 (2H, s); 6.64 (1H,dd); 6.76(1H,d); 7.12 (1H, dd); 7.19–7.39 (20H, m).

N-benzyloxycarbonyl-3-benzyloxy-4-dibenzylphosphonyloxy-L-phenylalanine 2-phenylethyl ester as a chromatographically pure oil (thin layer chromatography - eluent, petroleum ether: ethyl acetate=65:35, I$_2$ vapours detection).

N-benzyloxycarbonyl-3-benzyloxy-4-dibenzylphosphonyloxy-L-phenylalanine isopropyl ester as a chromatographically pure oil (thin layer chromatography - eluent, petroleum ether: ethyl acetate=65:35, $I_2$ vapours detection).

N-benzyloxycarbonyl-3-benzyloxy-4-dibenzylphosphonyloxy-L-phenylalanine cyclohexyl ester as a chromatographically pure oil (thin layer chromatography - eluent, petroleum ether: ethyl acetate=65:35, $I_2$ vapours detection).

EXAMPLE 5

Preparation of 3-hydroxy-4-phosphonyloxy-L-phenylalanine ethyl ester

A suspension of N-benzyloxycarbonyl-3-benzyloxy-4-dibenzyl phosphonyloxy-L-phenylalanine ethyl ester (23 g; 32.4 mmoles) prepared as described in Example 4, 10% palladium on charcoal (2.3 g) in a mixture of ethanol (250 ml) and water (50 ml) is kept at a pressure of 3-4 hydrogen atmospheres until theoretical absorption.

The catalyst is filtered off, the solvent is evaporated and the residue is crystallized from a mixture of ethyl alcohol : water = 1:2.

3-hydroxy-4-phosphonyloxy-L-phenylalanine ethyl ester melting at 162°-166° C. is obtained by filtration.

$^1$H-NMR (300 MHz, $D_2O$) delta (ppm): 1.27 (3H, t); 3.09-3.31 (2H, m); 3.59-3.68 (1H, m); 4.30 (2H, q); 6.78 (1H, dd); 6.85 (1H, d); 7.22 (1H, d).

Working in a similar manner the following compounds were obtained:

4-hydroxy-3-phosphonyloxy-L-phenylalanine ethyl ester m.p. 197°-200° C.

$^1$H-NMR (300 MHz, $D_2O$) delta (ppm): 1,27 (3H, t); 3.08-3.32 (2H, m); 4.28 (2H, q); 4.36 (1H, m); 6.90-6.96 (2H, m), 7.16 (1H, s).

L-dopa 4-O-ethylphosphate ethyl ester having a m.p. higher than 203° C. (dec.)

$^1$H-NMR (300 MHz, $D_2O$) delta (ppm): 1.22-1.29 (6H, m); 3.10-3.28 (2H, m); 4.04 (2H, quintet); 4.24-4.35 (3H, m); 6.78 (1H, dd); 6.85 (1H, d); 7.22 (1H, dd).

3-hydroxy-4-phosphonyloxy-L-phenylalanine n.butyl ester m.p. 184°-186° C. (from water/ethyl alcohol)

$^1$H-NMR (300 MHz, DMSO-$d_6$) delta (ppm) 0.88 (3H, t); 1.29 (2H, sextet); 1.52 (2H, quintet); 2.92 (2H, d); 4.10 (2H, t); 4.19 (1H, t); 6.47 (1H, dd); 6.49 (1H, d); 6.75 (1H, dd).

3-hydroxy-4-phosphonyloxy-L-phenylalanine 2-phenylethyl ester m.p. 184°-190° C. (from water/ethyl alcohol)

$^1$H-NMR (300 MHz, DMSO-$d_6$) delta (ppm) 2.71-2.82 (2H, m); 2.86 (2H, t); 3.86 (1H, t); 4.18-4.31 (2H, m); 6.34 (1H, dd); 6.52 (1H, d); 6.74 (1H, d); 7.12-7.31 (5H, m).

3-hydroxy-4-phosphonyloxy-L-phenylalanine isopropyl ester m.p. 165°-175° C. (from water/ethyl alcohol)

$^1$H-NMR (300 MHz, $D_2O$) delta (ppm) 1.28 (6H, d); 3.08-3.31 (2H, m); 4.31 (1H, t); 5.11 (1H, quintet); 6.75 (1H, dd); 6.81 (1H, d); 7.15 (1H, d).

3-hydroxy-4-phosphonyloxy-L-phenylalanine cyclohexyl ester m.p. 198°-200° C. (from water/ethyl alcohol)

$^1$H-NMR (300 MHz, DMSO-$d_6$) delta (ppm) 1.20-1.78 (m, 10H); 2.82-2.97 (2H, m); 4.15 (1H, t); 4.68-4.76 (1H, m); 6.45 (1H, dd); 6.55 (1H, d); 6.75 (1H, d).

EXAMPLE 6

Preparation of N-(N-benzyloxycarbonyl-gamma-L-glutamyl-alpha ethyl ester)-3-hydroxy-4-phosphonyloxy-L-phenyllanine ethyl ester sodium salt To a solution of 3-hydroxy-4-phosphonyloxy-L-phenylalanine ethyl ester (4 g; 13.1 mmoles), prepared as described in Example 5, and $NaHCO_3$ (1.1 g; 13.1 mmoles) in water (80 ml), a solution of N-benzyloxycarbonyl-L-glutamic-alpha-ethyl ester gamma-N-hydroxysuccinimide ester acid (6.39 g; 15.7 moles) in ethanol (80 ml) is added After 2 hours, the solution is concentrated to small volume and a saturated solution of NaCl is added to the residue; the product which solidifies is filtered, washed with a saturated solution of NaCl, with ethyl ether and then, suspended under stirring in acetone. The salt is discharged by filtration, the solution is evaporated to dryness; ethyl ether is added to the residue and the mixture is filtered. N-(N-benzyloxycarbonyl-gamma-L-glutamyl-alpha ethyl ester)-3-hydroxy-4-phosphonyloxy-L-phenyl-alanine ethyl ester sodium salt is thus obtained and used in the next step as it is.

$^1$H-NMR (300 MHz, DMSO-$D_6$) delta (ppm): 1.12 (3H, t); 1.18 (3H, t); 1.68-1.96 (2H, m); 2.19 (2H, t); 2.70-2.87 (2H, m); 3.98-4.12 (3H, m); 4.28-4.35 (1H, m); 5.05 (2H, m), 6.46 (1H, dd); 6.55 (1H, d); 6.69 (1H, d).

Working in a similar manner the following compounds were obtained:

N-(N-benzyloxycarbonyl-gamma-L-glutamyl-alpha ethyl ester)-3-hydroxy-4-ethylphosphonyloxy-L-phenylalanine ethyl ester ammonium salt as chromatographically pure oil (thin layer chromatography - eluent, n.butanol:acetic acid:water:toluene: acetone = 1:1:1:1:1, U.V. light, $I_2$ vapours detection).

$^1$H-NMR (300 MHz, DMSO-$d_6$) delta (ppm): 1.02-1.18 (9H, m); 1.68-1.96 (1H, m); 2.19 (2H, t); 2.71-2.88 (2H, m); 3.45 (1H, m); 3.76 (2H, quintet); 3.96-4.11 (6H, m); 4.28-4.35 (1H, m); 5.02 (2H, m); 6.48 (1H, dd); 6.56 (1H, d); 6.66 (1H, dd).

N-(N-benzyloxycarbonylglycyl)3-hydroxy-4-phosphonyloxy-L-phenylalanine ethyl ester ammonium salt as a chromatographicaly pure oil pure oil (thin layer chromatography - eluent, n.butanol:acetic acid:water:toluene:acetone = 1:1:1:1:1,, U.V. light, $I_2$ vapours detection).

N-(N-benzyloxycarbonylglycyl)-4-hydroxy-3-phosphonyloxy-L-phenylalanine ethyl ester ammonium salt as a chromatographicaly pure oil (thin layer chromatography - eluent, n.butanol:acetic acid:water:toluene:acetone = 1:1:1:1:1, U.V. light, $I_2$ vapours detection).

N-(N-benzyloxycarbonyl-L-alanyl)-3-hydroxy-4-phosphonyloxy-L-phenylalanine ethyl ester ammonium salt as a chromatographically pure oil (thin layer chromatography - eluent, n.butanol : acetic acid:water:- toluene:acetone=1:1:1:1:1, U.V. light, I$_2$ vapours detection).

$^1$H-NMR (300 MHz, D$_2$O) delta (ppm): 1.05-1.08 (3H, m); 1.26 (3H, s); 2.80-3.10 (2H, m); 3.65 (1H, q); 4.06-4.18 (2H, m); 5.12 (2H, s); 6.62-6.74 (2H, m); 7.08 (1H, d); 7.28-7.40 (5H, m).

N-(N-benzyloxycarbonyl-L-Leucyl)-3-hydroxy-4-phosphonyloxy-L-phenylalanine ethyl ester amonium salt as a chromatographically pure oil (thin layer chromatography pure oil (thin layer chromatography - eluent, n.butanol: acetic acid:water:toluene:acetone=1:1:1:1:1, U.V. light, I$_2$ vapours detection).

EXAMPLE 7

Preparation of N-(gamma-L-glutamyl-alpha-ethyl ester)-3-hydroxy-4-phosphonyloxy-L-phenylalanine ethyl ester sodium salt A suspension of N-(N-benzyloxycarbonyl-gamma-L-glutamyl-alpha-ethyl ester)-3-hydroxy-4-phosphonyloxy-L-phenylalanine ethyl ester sodium salt (7.3 g; 11.8 mmoles), prepared as disclosed in Example 6, and 10% Pd on charcoal (1.4 g) in 80% ethanol (200 ml) is kept at a pressure of 3-4 hydrogen atmospheres until theoretical absorption.

The catalyst is filtered off, the solvent is evaporated and the residue is suspended in acetone, filtered and recrystallized from 95% ethanol obtaining N-(gamma-L-glutamyl-alpha-ethyl ester)-3-hydroxy-4-phosphonyloxy-L-phenylalanine ethyl ester sodium salt melting at 139°-143° C.

$^1$H-NMR (300 MHz, DMSO-d$_6$) delta (ppm): 1.26 (3H, t); 1.28 (3H, t); 1.88-2.08 (2H, m); 2.3-2.48 (2H, m); 2.82-2.91 (1H, m); 3.18-3.25 (1H, m); 3.8 (1H, t); 4.18-4.31 (2H, m); 4.68-4.73 (1H, m); 6.71-6.76 (2H, m); 7.07 (1H, d).

Working in a similar manner the following compounds were obtained:

N-(gamma-L-glutamyl-alpha-ethyl ester)-3-hydroxy-4-ethyl phosphonyloxy-L-phenylalanine ethyl ester sodium salt, m.p. 90° C. (slow decomposition).

$^1$H-NMR (300 MHz, D$_2$O) delta (ppm): 1.20-1.28 (9H, m); 1.85-2.07 (2H, m); 2.38 (2H, t); 2.88-2.96 (1H, m); 3.12-3.20 (1H, m); 3.64 (1H, t); 4.02 (2H, quintet); 4.21 (4H, quintet); 4.63-4.68 (1H, m); 6.78 (1H, dd); 6.83 (1H, d); 7.18 (1H, dd).

N-(N-acetyl-L-methionyl)-3-hydroxy-4-phosphonyloxy-L-phyenylalanine ethyl ester m.p. 115°-120° C.

$^1$H-NMR (300 MHz, D$_2$O) delta (ppm): 1.22 (3H, t); 1.74-1.98 (2H, m); 1.99 (3H, s); 2.06 (3H, s); 2.32-2.54 (2H, m); 2.9-3.0 (1H, m); 3.12-3.25 (1H, m); 4.18 (2H, q); 4.19-4.38 (1H, m); 4.62-4.68 (1H, m); 6.73 (1H, dd); 6.82 (1H, d); 7.18 (1H, d).

N-glycyl-3-hydroxy-4-phosphonyloxy-L-phenylalanine ethyl ester m.p. 224°-227° C.

$^1$H-NMR (300 MHz, D$_2$O) delta (ppm): 1.29 (3H, t); 2.91-2.94 (1H, m); 3.18-3.23 (1H, m); 3.73 (2H, s); 4.24 (2H, q); 4.68-4.80 (1H, m); 6.73-6.79 (2H, m); 7.08 (1H, d).

N-glycyl-4-hydroxy-3-phosphonyloxy-L-phenylalanine ethyl ester m.p. 210°-213° C.

$^1$H-NMR (300 MHz, D$_2$O) delta (ppm): 1.24 (3H, t); 2.92-2.99 (1H, m); 3.18-3.23 (1H, m); 3.73 (2H, s); 4.24 (2H, q); 4.68-4.80 (1H, m); 6.73-6.79 (2H, m); 7.08 (1H, d).

N-glycyl-4-hydroxy-3-phosphonyloxy-L-phenylalanine ethyl ester m.p. 210°-213° C.

$^1$H-NMR (300 MHz, D$_2$O) delta (ppm): 1.24 (3H, t); 2.92-2.99 (1H, dd); 3.15-3.22 (1H, dd); 3.80 (2H, s); 4.22 (2H, d); 4.82 (1H, m); 6.92 (2H, bs); 7.10 (1H, s).

N-(L-alanyl)-3-hydroxy-4-phosphonyloxy-L-phenylalanine ethyl ester m.p. 199°-203° C.

$^1$H-NMR (300 MHz, D$_2$O) delta (ppm): 1.23 (3H, t); 1.49 (3H, t); 2.96-3.04 (1H, dd); 3.16-3.22 (1H, dd); 4.02 (1H, q); 4.21 (1H, q); 4.69 (1H, m); 6.78 (1H, dd); 6.85 (1H, d); 7.19 (1H, d).

N-Leucyl-3-hydroxy-4-phosphonyloxy-L-phenylalanine ethyl ester m.p. 217°-219° C.

$^1$H-NMR (300 MHz, D$_2$O) delta (ppm): 0.94 (3H,t); 1.26 (3H, t); 1.56 (2H, d); 2.91-2.98 (1H, dd); 3.17-3.25 (1H, dd); 3.87 (1H, t); 4.22 (2H, q); 4.75 (1H, m); 6.75 (1H, d); 6.78 (1H, d); 7.08 (1H, d).

We claim:

1. A compound of the formula

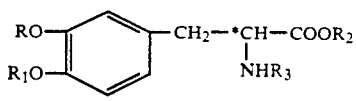

wherein
the asymmetric carbon atom marked with an asterisk has S configuration, and either R or R$_1$ is hydrogen and the other one is a group of the formula

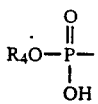

wherein
R$_4$ is hydrogen, phenyl, alkylphenyl or a C$_1$-C$_6$ alkyl optionally substituted by one to three groups selected from hydroxy, alkoxy, acyloxy, amino, carboxy or alkoxycarbonyl;

R$_2$ is a straight or branched C$_1$-C$_4$ alkyl, a C$_3$-C$_6$ cycloalkyl or a phenylalkyl having from 1 to 4 C atoms in the alkyl portion optionally substituted by 1 to 3 substituents selected from halogens, C$_1$-C$_3$ alkoxy and C$_1$-C$_3$ alkyl;

R$_3$ is hydrogen or an acyl group of a natural alpha-amino acid selected from glycine, alanine, valine, leucine, isoleucine, serine, threonine, cysteine, cystine, methionine, proline, hydroxyproline, phenylalanine, tyrosine, tryptophan, arginine, lysine, and histidine, optionally N-acylated by a C$_1$-C$_4$ acyl, or an acyl group of a natural aminoacid ester of the formula

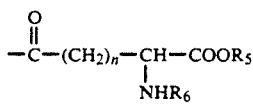

or

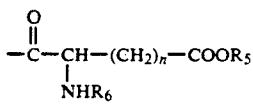

wherein
n is 1 or 2;
$R_5$ is hydrogen or a $C_1$-$C_3$ acyl;
$R_6$ is hydrogen or a $C_1$-$C_4$ acyl; or a salt thereof with pharmaceutically acceptable acid or base.

2. A compound according to claim 1, wherein $R_4$ is hydrogen, methyl, ethyl, isopropyl, phenyl or benzyl; $R_2$ is methyl, ethyl, isopropyl, butyl, isobutyl, cyclopentyl, cyclohexyl, 2-phenylethyl or 3-(4-methoxy-phenyl)-propyl; and $R_3$ is hydrogen or an acyl group of a natural alpha-amino acid selected from glycine, alanine, leucine and methionine or an acyl group of a natural acidic aminoacid ester of the formula

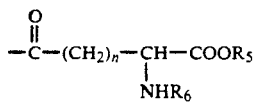

wherein
n = 2 and
$R_6$ is hydrogen.

3. A pharmaceutical composition containing a therapeutically active amount of a compound of the formula

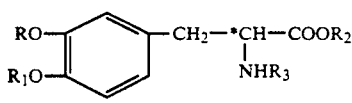  (I)

wherein
the asymmetric carbon atom marked with an asterisk has S configuration, and either R or $R_1$ is hydrogen and the other one is a group of the formula

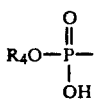

wherein
$R_4$ is hydrogen, phenyl, alkylphenyl or a $C_1$-$C_6$ alkyl optionally substituted by one to three groups selected from hydroxy, alkoxy, acyloxy, amino, carboxy or alkoxycarbonyl;
$R_2$ is a straight or branched $C_1$-$C_4$ alkyl, a $C_3$-$C_6$ cycloalkyl or a phenylalkyl having from 1 to 4 C atoms in the alkyl portion and is optionally substituted by 1 to 3 substituents selected from halogens, $C_1$-$C_3$ alkoxy and $C_1$-$C_3$ alkyl;
$R_3$ is hydrogen or an acyl group of a natural alpha-amino acid selected from glycine, alanine, valine, leucine, isoleucine, serine, threonine, cysteine, cystine, methionine, proline, hydroxyproline, phenylalanine, tyrosine, tryptophan, arginine, lysine, and histidine, optionally N-acylated by a $C_1$-$C_4$ acyl, or an acyl group of a natural amino aid ester of the formula

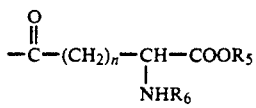

or

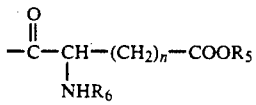

wherein
n is 1 or 2;
$R_5$ is a $C_1$-$C_3$ alkyl;
$R_6$ is hydrogen or a $C_1$-$C_4$ acyl;
or a salt thereof with pharmaceutically acceptable acid or base, optionally together with one or more excipients suitable for pharmaceutical use.

4. A pharmaceutical composition according to claim 3, wherein $R_4$ is hydrogen, methyl, ethyl, isopropyl, phenyl or benzyl; $R_2$ is methyl, ethyl, isopropyl, butyl, isobutyl, cyclopentyl, cyclohexyl, 2-phenylethyl or 3-(4-methoxy-phenyl)-propyl; and $R_3$ is hydrogen or an acyl group of a natural alpha-amino acid selected from glycine, alanine, leucine and methionine or an acyl group of a natural acidic amino acid ester of the formula

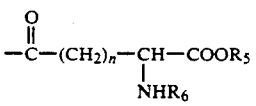

wherein
n = 2 and
$R_6$ is hydrogen.

5. A process for therapy for Parkinson disease and of cardiovascular diseases, which comprises administering an effective amount of a pharmaceutical composition according to claim 3 to one afflicted with such disease.

* * * * *